United States Patent [19]

Suzuki

[11] 4,318,884
[45] Mar. 9, 1982

[54] DISTRIBUTING NOZZLE WITH COOPERATING IONIC DETECTOR

[75] Inventor: Nobuyoshi Suzuki, Hachioji, Japan

[73] Assignee: Olympus Optical Co., Ltd., Tokyo, Japan

[21] Appl. No.: 210,362

[22] Filed: Nov. 25, 1980

[30] Foreign Application Priority Data

Dec. 7, 1979 [JP] Japan .................................. 54-157948

[51] Int. Cl.³ ...................... G01N 1/14; G01N 27/26
[52] U.S. Cl. ........................................ 422/63; 422/68; 422/100
[58] Field of Search ................... 422/68, 50, 63, 100; 204/1 T, 195 R

[56] References Cited

U.S. PATENT DOCUMENTS

| | | | |
|---|---|---|---|
| 3,607,094 | 9/1971 | Beer | 422/63 |
| 3,622,279 | 11/1971 | Moran | 422/65 |
| 3,707,455 | 12/1972 | Derr et al. | |
| 4,049,382 | 9/1977 | Ross, Jr. et al. | 422/68 |
| 4,130,394 | 12/1978 | Negersmith | 422/100 X |
| 4,228,831 | 10/1980 | Kerns | |

*Primary Examiner*—Ronald Serwin
*Attorney, Agent, or Firm*—Stevens, Davis, Miller & Mosher

[57] ABSTRACT

The disclosed distributing nozzle sucks liquid from a first vessel and discharges the sucked liquid into a second vessel, which distributing nozzle has an ionic sensor formed an insulated-gate field-effect transistor to measure specified ionic concentration of the liquid.

7 Claims, 7 Drawing Figures

DISTRIBUTING NOZZLE WITH COOPERATING IONIC DETECTOR

BACKGROUND OF THE INVENTION

1. Field of the Invention

This invention relates to a distributing nozzle to transfer a certain amount of liquid sample from a sample cup into a reaction vessel in an automatic analyzing device for quantitative analyses of specified ingredients in the sample, e.g., serum or urine. More particularly, the invention relates to a distributing nozzle of the aforesaid type which is provided with a function of measuring ionic concentration of the sample.

2. Description of the Prior Art

An automatic analyzing device generally uses a sample-distributing unit with a distributing nozzle to transfer a certain amount of liquid sample, e.g., serum taken from a patient, from a sample cup to one or more reaction vessels moving along a predetermined path. A reagent distributor selectively transfers reagents from a plurality of reagent vessels into the reaction vessel or vessels to produce reacting solution or solutions, depending on desired item or items of analysis. The absorbancy of the reacting solution is measured by a colorimeter during the reaction or after completion of the reaction. In the automatic analyzing device of the aforesaid type, it has been contemplated these days to measure various ionic concentrations in the sample, in addition to the quantitative analyses of the specified ingredients in the sample. To this end, it has been proposed to dip an ionic sensor consisting of a reference electrode and a glass electrode into the sample either at the sample cup or at the reaction vessel before or after the transfer of the sample to the reaction vessel. The proposed means to measure the ionic concentration has shortcomings in that a separate measuring means of the ionic concentration must be provided, that a special mechanism is necessary to dip the reference electrode and the glass electrode of the ionic sensor in the sample at the sample cup or the reaction vessel, and that the analyzing device accordingly becomes complicated in construction and operation and its size tends to become large.

SUMMARY OF THE INVENTION

Thereefore, an object of the present invention is to obviate the aforementioned shortcomings of the prior art. The inventors noted a recent development of ionic sensor which uses an insulated-gate field-effect transistor. The developed ionic sensor uses a field-effect transistor having a gate to which electrically-insulating ion-sensing membranes sensitive to specific ions, such as $SiO_2$, $Si_3N_4$ and the like, are selectively applied. The field-effect transistor may have a semi-conductor substrate with one ion-sensing membrane responsive to one kind of ion applied thereto, or may have a semi-conductor substrate with a plurality of ion-sensing membranes responsive to plural kinds of ions applied thereto. In other words, the latter has a plurality of insulated-gates formed thereon. Either of the aforesaid types of ionic sensors can be easily produced by a process commonly used in the semi-conductor industry. The ionic sensors formed of the insulated-gate field-effect transistors are characterized by excellent durability and small size.

To fulfill the object, the present invention provides a distributing nozzle which includes an ionic sensor formed of the aforesaid insulated-gate field-effect transistor, so that specified ionic concentration of the sample can be measured simultaneously with distribution or transfer of the sample, whereby the aforesaid shortcomings of the prior art are obviated.

A distributing nozzle according to the present invention sucks liquid contained in a first vessel and discharges the sucked liquid into a second vessel, which distributing nozzle has an ionic sensor formed of an insulate-gate field-effect transistor mounted at such portion of said distributing nozzle that comes in contact with said liquid, whereby specified ionic concentration of the liquid is measured as said liquid is sucked and discharged by said distributing nozzle, either at a moment when said distributing nozzle is dipped in said liquid in said first vessel or at a moment when the liquid is sucked in said distributing nozzle.

BRIEF DESCRIPTION OF THE DRAWINGS

For a better understanding of the invention, reference is made to the accompanying drawings, in which.

Like parts are designated by like numerals and symbols throughout different views of the drawings.

DESCRIPTION OF THE PREFERRED EMBODIMENTS

Figure 1:
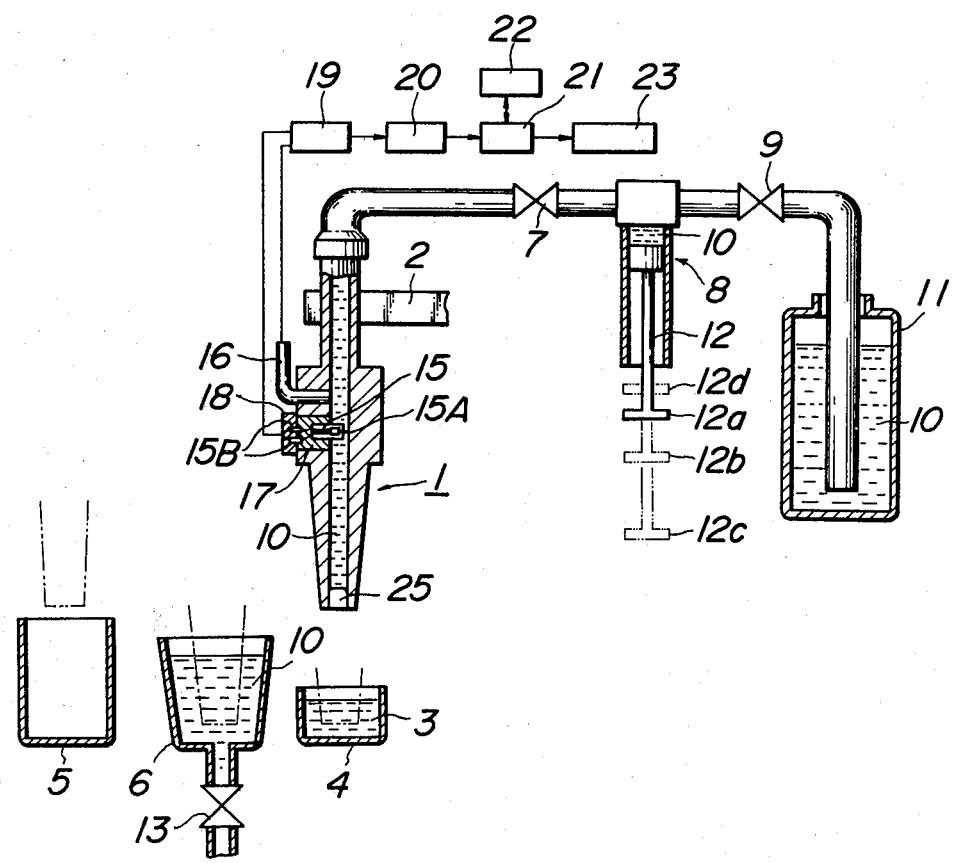
FIG. 1 is a schematic diagram showing the formation of a distributing means using an embodiment of the distributing nozzle of the invention.

Referring to FIG. 1 showing the formation of an embodiment of a distributing means using a distributing nozzle of the invention, a distributing nozzle 1 is detachably mounted to a holder 2. A moving means which is not shown moves the distributing nozzle 1 through the holder among three positions; i.e., a sample-sucking position where a sample cup 4 holding sample 3 such as serum lies, a sample discharging position where a reaction vessel 5 is located, and a nozzle-washing position where a washing vessel 6 is located. The moving means also vertically moves the distributing nozzle 1 and the holder 2 at the sample-sucking position and at the nozzle-washing position, so that the tip of the distributing nozzle 1 can come in the sample cup 4 and the washing vessel 6. The distributing nozzle 1 is for instance made of insulating synthetic resin. The top of the distributing nozzle 1 is connected to a washing solution vessel 11 through a valve 7, a syringe pump 8, and another valve 9. In the illustrated embodiment, the washing liquid vessel 11 holds standard solution 10 having a know low ionic concentration. The syringe pump 8 has a piston 12 which is reciprocated for instance by a driving motor (not shown). The washing vessel 6 is connected to a drain vessel (not shown) through a valve 13.

The distributing means of FIG. 1 sucks a certain amount of the sample 3 from the sample cup 4 by the distributing nozzle 1 and discharge the thus sucked sample into the reaction vessel 5. The distributing nozzle 1 of this embodiment has an ionic sensor 15 formed of an insulated-gate field-effect transistor and a reference electrode 16 embedded at suitable points in that area which is covered by the sample 3 when the aforesaid amount of the sample 3 is sucked by the distributing nozzle 1. The ionic sensor 15 has at least one ion-sensing portion (insulated-gate) 15A disposed so as to come in contact with the sample 3 sucked into the distributing nozzle 1, and source and drain electrodes of the ionic sensor 15 are connected to connection terminals 15B through lead wires. That portion of the distributing nozzle 1 which holds the ionic sensor 15 is molded by insulating resin 17. The connection terminals 15B are so arranged that a connector socket 18 can detachably engage that portion of the distributing nozzle 1 which carries the terminals 15B, whereby the terminals 15B are electrically connected to outside circuits through terminals of the connector socket 18. The reference electrode 16 is mounted on the distributing nozzle in such manner that a liquid-contact portion (not shown) of the reference electrode 16 comes in contact with the sample 3 sucked into the distributing nozzle 1. Output signals, e.g., in the form of voltage, from the ionic sensor 15 and the reference electrode 16 representing a detected ionic concentration of the sample 3 are stored in a memory 22 through an amplifier 19, an AD converter 20, and a controller 21 consisting of a computer or the like. Then, measured value for the standard solution 10 is operationally processed by the controller 21, and the measured value for the sample 3 stored in the memory 22 is calibrated by the thus processed value for the standard solution 10, and the calibrated correct result of the measured value for the sample 3 is indicated on a display 23.

The operation of the distributing means of FIG. 1 will be now described. When the distributing operation starts in this embodiment, an air layer 25 is present at the tip of the distributing nozzle 1, and passage from the distributing nozzle 1 to the washing solution vessel 11 is filled with the standard solution 10, while the lower end of the piston 12 of the syringe pump 8 is at a position 12a as shown by solid lines in FIG. 1. Under such conditions, the distributing nozzle 1 located at the sample-sucking position is lowered until the tip of the distributing nozzle 1 is dipped in the sample 3 in the sample cup 4. At this moment, the valve 7 is opened while the valve 9 is closed, and the lower end of the piston 12 of the syringe pump 8 is lowered to its lower position 12b to suck a predetermined amount of the sample 3 into the distributing nozzle 1. Then, the distributing nozzle 1 is raised and moved to the sample-discharging position where the reaction vessel 5 is located. During the period from the sucking of the sample 3 to the arrival at the sample-discharging position, specified ionic concentration of the sample 3 sucked in the distributing nozzle 1 is measured by the ionic sensor 15, and the output voltage from the ionic sensor 15 representing the value of the specified ionic concentration of the sample 3 is stored in the memory 22.

With the distributing nozzle 1 at the sample-discharging position, the lower end of the piston 12 of the syringe pump 8 is raised to the position 12a, so as to discharge the sucked sample 3 into the reaction vessel 5. The distributing nozzle 1 is then moved to the nozzle-washing position where the washing vessel 6 is located, and the distributing nozzle 1 is lowered until its tip enters into the washing vessel 6. During this movement, the valve 7 is closed while the valve 9 is opened, and the lower end of the piston 12 of the syringe pump 8 is lowered to its lowermost position 12c, so as to suck a predetermined amount of the standard solution 10 into the syringe pump 8. After the sucking, the valve 7 is opened while the valve 9 is closed, and the lower end of the piston 12 of the syringe pump 8 is raised to its uppermost position 12d, so as to discharge the sucked solution 10 into the washing vessel 6. At this moment, the valve 13 connected to the washing vessel 6 is kept closed. Thus, the discharged standard solution 10 effectively washes the inner surface of the distributing nozzle 1, the ionic sensor 15, and the reference electrode 16. Besides, the discharged standard solution 10 is kept in the washing vessel 6, so that the outer surface of the tip portion of the distributing nozzle 1, i.e., the portion dipped in the sample 3 before, is now effectively washed. After the distributing nozzle 1 is washed, the valve 13 is opened to drain the standard solution 10 in the washing vessel 6 to the drain vessel (not shown).

Finally, the lower end of the piston 12 of the syringe pump 8 is slightly lowered to its position 12a, so as to form the air layer 25 at the tip of the distributing nozzle 1, while the distributing nozzle 1 is raised and moved to the sample-sucking position. Thus, one cycle of the sample transfer is completed, and the distributing means is now ready for next cycle of operations. Before sucking the next sample, the ionic concentration of the standard solution 10 in the distributing nozzle 1 after the washing is measured, the controller 21 processes the thus measured value to calibrate the measured value for the sample 3 stored in the memory 22 by using the measured value of the standard solution 10, and the correct measured value for the sample 3 is indicated on the display 23.

Thereafter, specified ionic concentration of each sample can be measured successively during the succeeding distributing process thereof, by successively repeating the aforesaid operation in proper sequence.

Modified examples of the distributing nozzle according to the present invention will be now described.

Figure 2:
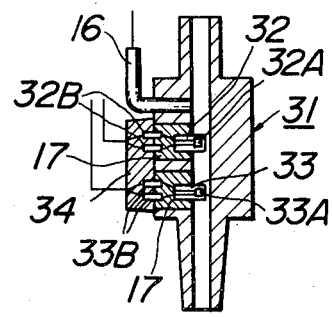
FIGS. 2, 3 and 4 are schematic sectional views showing different modifications of the distributing nozzle of the invention.
Figure 3:
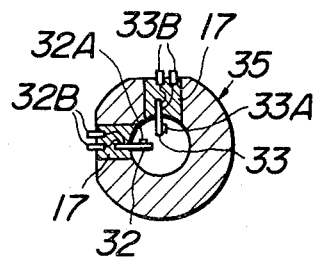

FIG. 2 shows a distributing nozzle 31 which is different from the distributing nozzle 1 of FIG. 1 in that two ionic sensors 32 and 33 formed of insulated-gate field-effect transistors are mounted on the distributing nozzle 31 to measure different ionic concentrations. The ion-sensing portions 32A and 33A of the ionic sensors 32 and 33 are mounted so as to come in contact with each sample 3 sucked into the distributing nozzle 31, while keeping a spacing therebetween in the direction of longitudinal axis of the distributing nozzle 31. Connection terminals 32B and 33B of the ionic sensors 32 and 33 are connected to an amplifier (not shown in FIG. 2) through a common connector socket 34. The remaining portions of the construction of the distributing nozzle 31 are the same as those of the distributing nozzle 1 of the preceding embodiment. The two ionic sensors 32 and 33 may be radially disposed with an angular displacement therebetween on a plane perpendicular to the longitudinal axis of a distributing nozzle 35, as shown in FIG. 3.

Figure 4:
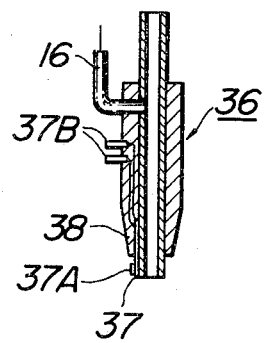

FIG. 4 illustrates another distributing nozzle 36 which is different from the preceding embodiments in that an ionic sensor 37 formed of an insulated-gate field-effect transistor is mounted on the outer peripheral surface of tip portion of the distributing nozzle. The ionic sensor 37 is enclosed by a molding of insulating resin 38 except an ion-sensing portion 37A thereof, and source and drain electrodes of the ionic sensor 37 are connected to one ends of lead wires embedded in the insulating resin 38, the opposite ends of the lead wires being connected to connection terminals 37B exposed to the outside at a position which is not dipped in the sample 3. The distributing nozzle 36 measures the ionic concentration of the sample 3 when the tip of the distributing nozzle 36 is dipped in the sample 3 for suction thereof. Once the suction is started, both the ion-sensing portion 37A of the ionic sensor 37 and the reference electrode 16 are simultaneously in contact with the sample 3. The ionic concentration of the standard solution 10 is measured, for instance, during washing of the distributing nozzle 36, when both the ion-sensing portion 37A of the ionic sensor 37 and the reference electrodre 16 are simultaneously in contact with the standard solution 10. It is noted that a plurality of the ionic sensors may be mounted on the outer surface of the distributing nozzle at the tip thereof to measure different kinds of ionic concentrations.

In the examples described above, the reference electrode 16 is also mounted on the distributing nozzle. However, the reference electrode 16 can be used in common for measurement of different kinds of ionic concentrations, so that it can be mounted not on the distributing nozzle but at any suitable position on the passage communicating with the distributing nozzle, preferably at such a position which allows simultaneous contact of both the ion-sensing portion of the ionic sensor and the reference electrode with the sample sucked by the distributing nozzle.

Figure 5:
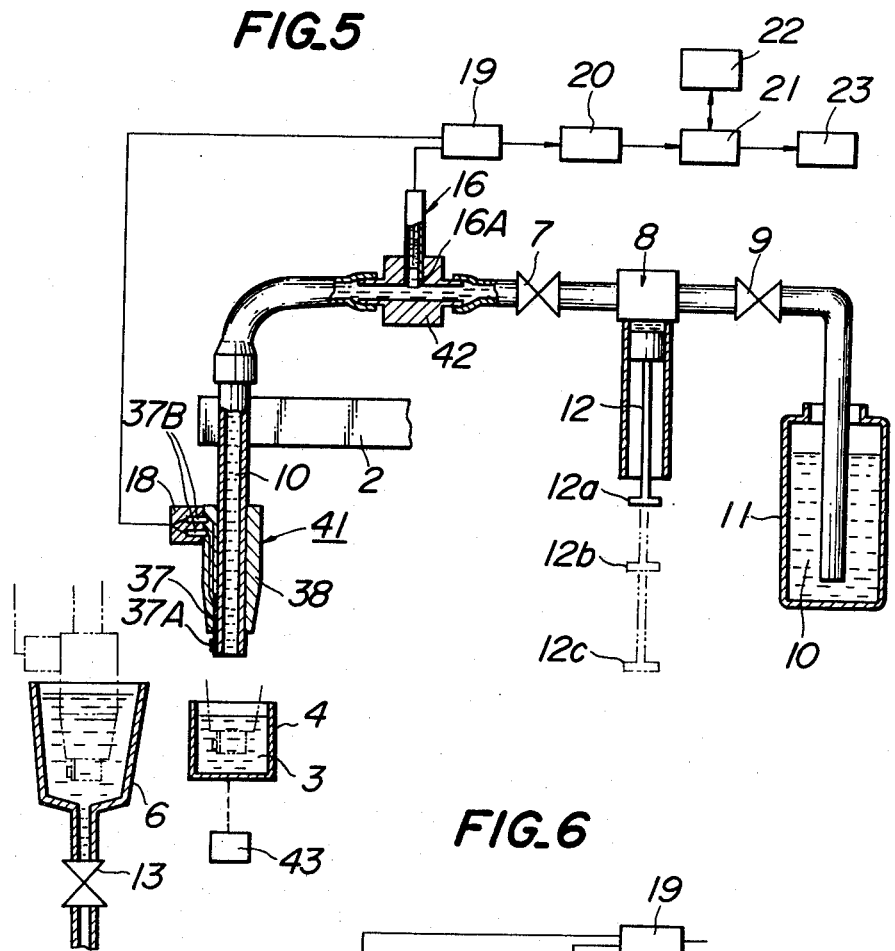
FIG. 5 is a schematic diagram showing another formation of a distributing means using a distributing nozzle of the invention.

FIG. 5 schematically shows the formation of another distributing means using a distributing nozzle 41 similar to the embodiment of FIG. 4. An electrode holder 42 is provided at a suitable position along a passage communicating with the distributing nozzle 41, and a reference electrode 16 is held by the electrode holder 42 so that a liquid-contact portion 16A of the reference electrode 16 can come in contact with the liquid in the passage. In the distributing means of FIG. 5, the distributing nozzle 41 is movable between a sample-sucking position and a nozzle-washing position, and the distributing nozzle 41 is vertically movable at each of the two positions. A sample cup 4 of this distributing means is rotatably supported and driven by a motor 43 to agitate the sample 3 carried by the sample cup 4 by the rotation.

The operation to measure specified ionic concentration in the distributing means of FIG. 5 will be now described. At the start of the ionic concentration measurement, the passage from the tip of the distributing nozzle 41 to a washing solution vessel 11 is filled with standard solution 10, while the lower end of the piston 12 of a syringe pump 8 is held at a position 12a as shown by solid lines. Under such conditions, the distributing nozzle 41 is lowered at the sample-sucked position, until the tip of the distributing nozzle 41 is dipped in the sample 3 in the sample cup 4. At this time, the sample cup 4 is rotated by the motor 43. Then, the valve 7 is opened while the valve 9 is closed, and the lower end of the piston 12 of the syringe pump 8 is lowered to a position 12b so as to suck a predetermined amount of the sample 3. After the suction, the valve 7 is closed while the valve 9 is opened, and the lower end of the piston 12 of the syringe pump 8 is further lowered to a position 12c, so as to suck a certain amount of the standard solution 10 into the syringe pump 8. During this period, the ion sensor 37 is dipped in the sample 3, so that specified ionic concentration of the sample 3 is measured and stored in a memory 22.

Then, the distributing nozzle 41 is raised and moved to the nozzle-washing position, where the distributing nozzle 41 is lowered until the tip thereof enters into a washing vessel 6. At this moment, the valve 7 is opened while the valve 9 is closed, and the lower end of the piston 12 of the syringe pump 8 is pushed up to the position 12a, whereby the previously sucked sample 3 and standard solution 10 are discharged into the washing vessel 6. During the discharge, a valve 13 connected to the washing vessel 6 is kept closed. Whereby, the inner and outer surfaces of the distributing nozzle 41, the ionic sensor 37, and the reference electrode 16 are washed. After the washing, the valve 13 is opened to drain the liquid in the washing vessel 6 to a drain vessel (not shown). The valve 13 is closed again after the draining. When the tip of the distributing nozzle 41 is still placed in the washing vessel 6, the valve 7 is closed while the valve 9 is opened, and the lower end of the piston 12 of the syringe pump 8 is lowered to its lowermost position 12c, so as to suck a predetermined amount of the standard solution 10 into the syringe pump 8. After the suction, the valve 7 is opened while the valve 9 is closed, and the lower end of the piston 12 of the syringe pump 8 is raised to its position 12a, so as to discharge the sucked standard solution 10 into the washing vessel 6 where the standard solution 10 is pooled. Thus, the ion-sensing portion 37A of the ionic sensor 37 mounted to the tip of the distributing nozzle 41 is dipped in the pooled standard solution 10, so that the ionic concentration of the standard solution 10 is measured, and the measured value is operationally processed by a controller 21, so as to calibrate the measured value for the sample 3 stored in the memory 22. The calibrated correct value of the measured ionic concentration of the sample 3 is indicated on a display 23.

After the measurement of the ionic concentration of the standard solution 10, the valve 13 is opened to drain the standard solution 10 from the washing vessel 6 to a drain vessel (not shown). At the same time, the distributing nozzle 41 is raised and moved to the sample-sucking position. Whereby, the distributing means is ready for the measurement of the next sample.

Specified ionic concentrations of the succeeding samples can be measured in the succeeding operations for distribution, by successively repeating the aforementioned measuring operation in proper sequence.

Figure 6:
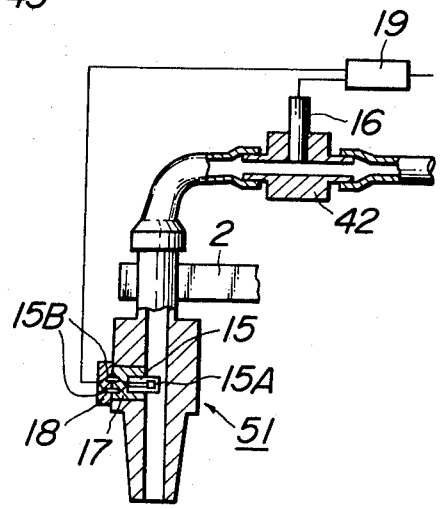
FIG. 6 is a schematic diagram showing an essential portion of a different distributing means using a distributing nozzle of the invention.

FIG. 6 schematically shows a distributing nozzle 51, which has an ionic sensor 15 mounted on a fluid passage of the distributing nozzle 51 as in the case of the embodiment of FIG. 1. The reference electrode 16 of the example of FIG. 6 is carried by an electrode holder 42 disposed along a passage communicating with the distributing nozzle 51 as in the case of the distributing means of FIG. 5. The distributing nozzle 51 can be used in a distributing means in a similar way to that of FIG. 1 or 5. The distributing nozzle 51 can be used to successively measure specified ionic concentrations of successive samples during their distributing processes, by effecting the measuring operations as described hereinbefore by referring to FIG. 1 and FIG. 5.

Figure 7:
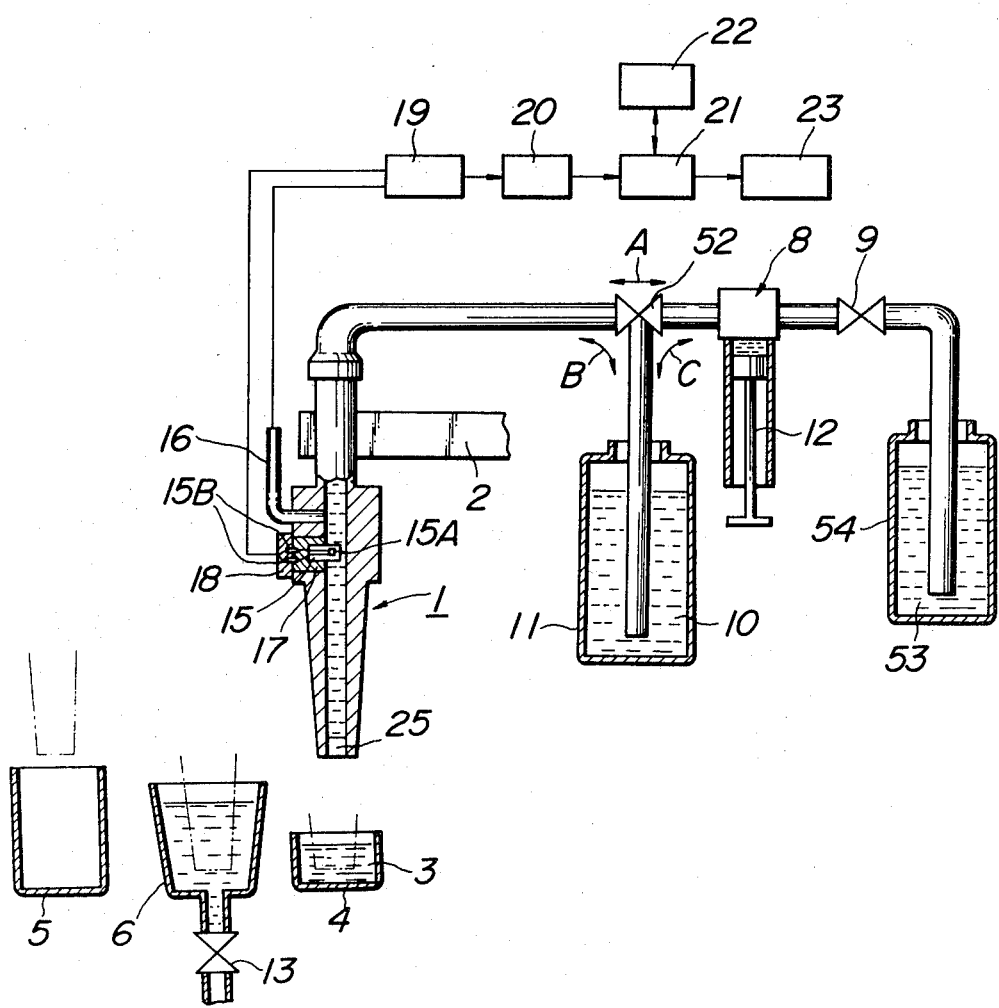
FIG. 7 is a schematic diagram showing the formation of a diluting means using a distributing nozzle of the invention.

It is noted that the distributing nozzle of the invention can be used to form a diluting means. FIG. 7 illustrates an embodiment of the diluting means using a distributing nozzle of the invention. In the figure, a distributing nozzle 1 is connected to a diluent vessel 54 containing diluent solution (for instance, ion exchange water) 53 through a cross valve 52, a syringe pump 8, and a valve 9. The remaining inlet opening of the cross valve 52 is connected to a washing solution vessel 11 holding standard solution 10. The remainder of the diluting means of FIG. 7 is the same as that of the distributing means of FIG. 1.

One way of carrying out dilution and distribution of sample by the diluting means of FIG. 7 is shown in Table 1.

as $Na^+$, $K^+$ and $Cl^-$ can be measured simultaneously. Moreover, a plurality of ion-sensing portions selectively responsive to different ions can be formed on one semiconductor substrate, so as to provide an ionic sensor responsive to the different ions.

What is claimed is:

1. A distributing nozzle for sucking liquid from a first

TABLE 1 (a) & (b)

| Step | Position of distributing nozzle 1 | Passing direction of cross valve 52 | Valve 9 | Valve 13 | Piston 12 of syringe pump 8 |
|---|---|---|---|---|---|
| Sucking sample | Sample-sucking position (nozzle tip in sample) | Arrow A | Close | Close | Withdraw by a predetermined stroke $S_1$ |
| Measuring ionic concentration of sample and sucking diluent | Sample-sucking position → sample-discharging position (nozzle tip in air) | Arrow A ↓ Arrow B | Open | " | Withdraw by a predetermined stroke $S_2$ |
| Discharging sample and diluent solution | Sample-discharging position | Arrow A | Close | " | Push in by the sum of preceding strokes ($S_1 + S_2$) |
| Sucking standard solution | Sample-discharging position → nozzle-washing position | Arrow C | " | " | Withdraw by a predetermined stroke $S_3$ |
| Washing distributing nozzle and measuring ionic concentration of standard solution | Nozzle-washing position (nozzle tip entering in washing vessel 6) | Arrow A | Close ↓ Open | Close | Push in by the predetermined stroke $S_3$ |
| Sucking diluent solution | Nozzle-washing position (nozzle tip entering in washing vessel 6) | Arrow B | Open | " | Withdraw by a predetermined stroke $S_4$ |
| Discharging diluent solution | Nozzle-washing position (nozzle tip entering in washing vessel 6) | Arrow A | Close | " | Push in by the predetermined stroke $S_4$ |
| Forming air layer at tip of distributing nozzle | Nozzle-washing position → sample-sucking position (nozzle tip in air) | " | " | Close | Withdraw slightly |

When diluting means is ready for sucking the sample, a passage from the distributing nozzle 1 to the diluent vessel 54 is filld with the diluent solution 53, while an air layer 25 is present at the tip of the distributing nozzle 1.

Specified ionic concentration of each of the successive samples can be successively measured in the step of sucking each sample and the diluent solution to dilute the sample, by repeating the operations of Table 1 in proper sequence.

As described in the foregoing, according to the present invention, the specified ionic concentration of the sample can be measured when the sample is distributed, without using any separate means for measuring the ionic concentration. Thus, the distributing nozzle of the present invention can be advantageously applied to an automatic analyzing device or the like apparatus, while facilitating the reduction of the size of the device. If the distributing nozzle is detachably mounted on a holder and if the connector socket is detachably applied to the connection terminals of the ionic sensor as shown in the embodiment of the invention, it is possible to prepare a plurality of distributing nozzles with different ionic sensors adapted to measure different kinds of ionic concentrations, so that any of a wide variety of different kinds of ionic concentrations can be measured simply by replacing the distributing nozzle being held by the holder.

The present invention is not restricted to the examples and embodiments described in the foregoing, but numerous modifications and changes are possible. For instance, although the illustrated embodiments are provided with only one or two ionic sensors, three or more ionic sensors can be mounted on one distributing nozzle of the invention, so that a number of different ions, such vessel and discharging the thus sucked liquid into a second vessel comprising, an ionic sensor formed of an insulated-gate field-effect transistor mounted at such portion of said distributing nozzle that comes in contact with said liquid, whereby specified ionic concentration of said liquid is measured as said liquid is sucked and discharged by said distributing nozzle.

2. A distributing nozzle as defined in claim 1, wherein said ionic sensor is adapted to measure said ionic concentration of said liquid when said distributing nozzle is dipped in said liquid at said first vessel to suck said liquid.

3. A distributing nozzle as defined in claim 1, wherein said ionic sensor is adapted to measure said ionic concentration of said liquid when said liquid is sucked in said distributing nozzle.

4. A distributing nozzle as defined in claim 1, wherein said distributing nozzle has at least one ionic sensor with ion-sensing portion thereof disposed on inside surface of the distributing nozzle.

5. A distributing nozzle as defined in claim 1, wherein said distributing nozzle has at least one ionic sensor with ion-sensing portion thereof disposed on outer surface of tip portion of the distributing nozzle.

6. A distributing nozzle as defined in claim 1, wherein said distributing nozzle has a molded portion made of insulating resin and said ionic sensor is embedded in said molded portion.

7. A distributing nozzle as defined in claim 6, wherein said molded portion has a connection terminal means connected to source and drain electrodes of said insulated-gate field-effect transistor of said ionic sensor through lead wires buried in said molded portion.

* * * * *